United States Patent [19]

Patzke et al.

[11] 4,430,435

[45] Feb. 7, 1984

[54] ASSAY SYSTEM

[75] Inventors: James V. Patzke; Burton J. Rosenberg, both of Raleigh, N.C.

[73] Assignee: Burroughs Wellcome Co., Research Triangle Park, N.C.

[21] Appl. No.: 220,105

[22] Filed: Dec. 24, 1980

[51] Int. Cl.³ .................... G01N 33/16; A61K 43/00; G01T 1/00

[52] U.S. Cl. ...................... 436/504; 424/1.1; 436/501; 436/503; 436/815; 436/816; 422/61

[58] Field of Search .................. 424/1, 1.5; 23/230 B; 436/501, 503, 504, 63, 804, 816, 901, 815; 422/61; 252/301.1

[56] References Cited

U.S. PATENT DOCUMENTS

| | | | |
|---|---|---|---|
| 3,928,553 | 12/1975 | Hollander | 424/1 |
| 4,108,974 | 8/1978 | Wegfahrt et al. | 424/1 |
| 4,160,818 | 7/1979 | Smith | 424/8 |
| 4,188,485 | 2/1980 | Kukla | 424/267 |
| 4,197,288 | 4/1980 | Snyder | 424/1 |
| 4,208,400 | 6/1980 | Edwards | 424/1 |
| 4,241,177 | 12/1980 | Singh | 435/7 |
| 4,273,778 | 6/1981 | Hadley | 260/239 BF |
| 4,280,993 | 7/1981 | Braestrup | 422/61 |
| 4,336,259 | 6/1982 | Hadley | 260/239 BF |

OTHER PUBLICATIONS

Borga, Olof, Clin. Pharmacol. Ther., vol. 22 (5 Part 1), pp. 539–544 (1977).

*Primary Examiner*—Brooks H. Hunt
*Assistant Examiner*—M. Moskowitz
*Attorney, Agent, or Firm*—Donald Brown

[57] ABSTRACT

The accuracy of assays for monitoring concentrations of basic drugs in biological fluids containing $\alpha_1$-acid glycoproteins, such as blood (serum or plasma), is improved by the addition of certain organic phosphate compounds to minimize the "protein effect." Kits containing the elements of the invention are also disclosed.

38 Claims, No Drawings

ASSAY SYSTEM

The present invention relates to assay procedures for drugs. More specifically it is concerned with the assay of drugs in biological fluids by means of competitive binding techniques.

Routine monitoring of drug therapy by measurement of plasma or serum concentrations is a valuable and widely used aid to clinical management. Amongst assays routinely employed for this purpose are assays based on a competitive binding technique in which the drug to be assayed and a labeled ligand compete for sites on a receptor material. Examples of such assays include for example radioimmunoassay, radioreceptor assay, enzyme immunoassay and fluorescent immunoassay. Such techniques, however, may suffer disadvantages when applied to biological fluids such as serum or plasma because of a "protein effect" in which certain proteins, in particular $\alpha_1$-acid glycoprotein, in the biological fluid compete with the receptor agent for drug/labelled agent thereby giving erroneous results. Until now this problem was generally overcome by means of an inconvenient and time consuming separation of the protein and drug, normally by means of an extraction procedure.

It has now been found that certain organic phosphates will block the binding of drug and labelled ligands to interfering protein but not to receptor and thus inclusion of such compounds in such assays will minimize the "protein effect" and obviate the need for a separation procedure prior to the assay being carried out.

The invention accordingly provides a method of assaying a basic drug in a biological fluid containing an interfering protein which comprises the steps of:

(a) adding to the material to be assayed a receptor material, a labeled receptor binder (ligand) for the receptor material and a blocking (inhibiting) agent selected from a compound of formula (I):

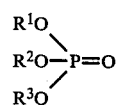

$$\begin{array}{c} R^1O \\ \phantom{R^2O-}\diagdown \\ R^2O-P=O \\ \phantom{R^3O}\diagup \\ R^3O \end{array} \quad (I)$$

wherein $R^1$, $R^2$ and $R^3$ may be the same or different and are each lower alkyl or lower alkoxy lower alkyl, the blocking agent being present in an amount sufficient to prevent binding to or to displace drug or receptor binder from interfering protein but insufficient to prevent binding to the receptor material;

(b) causing the drug and receptor binder to interact with the receptor material; and (c) determining the proportion of the receptor binding bound to the receptor material.

It has been noted in the literature [see for example O. Borga, et al., Clinical Pharmacol. Therap., 22, 539–544 (1977)] that tris(butoxyethyl) phosphate (TBEP) causes a redistribution of certain basic drugs between plasma and red blood cells and hence it was previously suggested that TBEP is to be avoided in such assays.

By the term "basic drug" is meant a drug which is positively charged at physiological pH. Examples of such drugs in which the use of a blocking agent in an assay procedure has been found particularly effective include neuroleptic agents (eg. haloperidol, fluphenazine, trifluperazine, chlorpromazine, thiothixene and thioridazine), tricyclic antidepressants (eg. amitriptyline, clomipramine, desipramine, imipramine and nortriptyline) and $\beta$-adrenergic drugs (eg. propranolol, alprenolol, practolol and oxprenolol).

The term "lower" as applied herein to alkyl or alkoxy refers to such groups containing from 1 to 4 carbon atoms. In the blocking agents of formula (I) $R^1$, $R^2$ and $R^3$ are conveniently the same; preferably $R^1$, $R^2$ and $R^3$ are all alkoxyalkyl groups. Suitable blocking agents include triethyl phosphate (TEP), tributyl phosphate (TBP) and, particularly, tris(butoxyethyl) phosphate (TBEP). The amount of blocking agent to be added will vary both with the particular agent used and the nature of the sample being assayed but may be readily determined. For human serum suitable quantities of TBEP are from about 2 µg to about 50 µg per 100 µl of sample, conveniently from about 5 to about 20 µg per 100 µl and preferably about 15 µg per 100 µl of sample.

The blocking agent may be added to the sample either before or after the addition of the other agents. By the term "interfering protein" is meant any protein in a biological fluid which binds a basic drug. Of such proteins the most important is $\alpha_1$-acid glycoprotein.

The blocking agents referred to may be employed in any assay based upon competitive binding. Such assays include for example radioimmunoassay, radioreceptor assay, enzyme immunoassay and fluorescent immunoassay.

Steps (b) and (c) of the method of the invention comprise conventional steps of competitive binding assays and may be carried out in any manner known in the art for conducting such assays; the reagents used will also be those employed in such conventional assays. Where a heterogeneous receptor assay is employed (for example radioimmunoassay or radioreceptor assay) an additional step of separating the bound or unbound receptor binder is generally included prior to carrying out step (c).

The method of the invention may be applied to the assay of basic drugs in any biological fluids in which interfering proteins such as $\alpha_1$-acid glycoprotein are present. Such biological fluids include blood plasma and serum.

The blocking agent may be provided as part of a test kit for carrying out competitive binding assays. The invention additionally provides a test kit as a mercantile unit comprising at least one container containing the following incredients:

a receptor material for a basic drug;

a labelled receptor binder for the receptor material; and a blocking agent as hereinbefore defined.

Each of the ingredients may also be packaged in one or more individual containers. Optionally a standard solution of the drug to be assayed and buffer may be included in the kit.

The invention further provides a composition of matter comprising:

a receptor material for a basic drug;

a basic drug;

a labelled receptor binder for a basic drug;

a blocking agent as hereinbefore defined; and a biological protein-containing fluid, suitably a human body fluid.

The following Examples illustrate the invention.

EXAMPLE 1

Effect of Blocking Agent on the "Protein Effect" in Drug Free Serum (a) Serum was obtained from 10 drug free individuals and the binding of $^3$H-spiperone to calf caudate (a system for neuroleptic drug radioreceptor assay) determined in both the absence and presence of tris(butoxyethyl) phosphate (TBEP) as a blocking agent.

To samples of serum (100 μl) in polypropylene tubes (12×55 mm) were added mixtures (500 μl) containing homogenised calf caudate (8 mg/ml) and $^3$H-spiperone (0.4 nM, 21 Ci/mmole) prepared as described by S. R. Lader J. Immunoassay, 1, 57–75 (1980). Where a blocking agent was used a solution of TBEP (100 μl; 100 μg/ml in water) was added prior to the addition of calf caudate/$^3$H-spiperone mixture. The tubes were incubated at 37° C. for 30 minutes, cold saline (2 ml) added, the mixture centrifuged, the supernatent discarded and the resultant pellet suspended with a scintillant (Aquasol; 2.5 ml) and counted for $^3$H in a liquid scintillation spectrometer. The percentage of bound and unbound $^3$H-spiperone was determined; the results are shown in Table I below. The results demonstrate that the between sample variability (CV) in $^3$H-spiperone binding is reduced in the presence of TBEP.

(b) The experiment described in (a) above was repeated but in each case a neuroleptic drug (haloperidol) was added to each serum sample prior to the assay to a known final concentration of 100 nM. The assay was then carried out as described above providing a measure of the recovery of the drug, i.e. the amount of drug found to be present by the assay in relation to the amount known to have been added. The results are shown in Table I. The results demonstrate that the variability (CV) in the recovery of added haloperidol is reduced by the presence of TBEP.

TABLE I

| Sample No. | % of $^3$H—Spiperone Bound | | Haloperidol Recovered (nM) | |
|---|---|---|---|---|
| | TBEP absent | TBEP present | TBEP absent | TBEP present |
| 1 | 23.8 | 31.9 | 101 | 96 |
| 2 | 26.6 | 32.2 | 78 | 102 |
| 3 | 23.5 | 31.5 | 131 | 112 |
| 4 | 30.0 | 33.8 | 23 | 81 |
| 5 | 28.7 | 33.5 | 43 | 102 |
| 6 | 29.5 | 32.8 | 32 | 118 |
| 7 | 23.0 | 32.2 | 147 | 122 |
| 8 | 25.3 | 31.8 | 96 | 134 |
| 9 | 24.3 | 31.9 | 90 | 110 |
| 10 | 26.6 | 32.8 | 62 | 83 |
| X | 26.1 | 32.4 | 80 | 106 |
| CV | 9.8% | 2.3% | 51% | 16% |

X is the mean of the samples assayed; CV is the coefficient of variation.

EXAMPLE 2

Reduction of "Protein Effect" by Phosphate Derivatives in Neuroletic Drug Radioreceptor Assay By the method described in Example 1(a) the effects of varying concentrations of phosphates [TBEP, triethyl phosphate (TEP) and tributyl phosphate (TBP)] or serum binding of $^3$H spiperone in serum were determined and compared to the binding in phosphate buffer with or without blocking agents in which the serum effect is absent. The results are shown in Table 2 to 4.

TABLE 2

The Effect of TBEP on the Binding of $^3$H-Spiperone to Calf Caudate in the Presence of Serum or Buffer.

| | % $^3$H—Spiperone Bound | | % Change | |
|---|---|---|---|---|
| μg/Tube TBEP | in Serum | in Buffer | in Serum | in Buffer |
| 0 | 23.0 | 36.3 | 0 | 0 |
| 1.25 | 23.0 | 35.0 | 0 | −4 |
| 2.50 | 26.2 | 35.3 | +14 | −3 |
| 5.00 | 27.8 | 35.6 | +21 | −2 |
| 10.00 | 29.1 | 32.5 | +27 | −10 |
| 20.00 | 27.2 | 32.4 | +18 | −11 |
| 40.00 | 26.1 | 31.6 | +13 | −13 |
| 80.00 | 24.3 | 27.7 | +6 | −24 |

TABLE 3

The Effect of Triethylphosphate on the Binding of $^3$H—Spiperone Calf Caudate in the Presence of Serum or Buffer.

| | % $^3$H—Spiperone Bound | | % Change | |
|---|---|---|---|---|
| μg/Tube TBEP | in Serum | in Buffer | in Serum | in Buffer |
| 0 | 23.6 | 37.8 | 0 | 0 |
| 50 | 27.8 | 37.9 | +18 | 0 |
| 100 | 28.6 | 37.5 | +21 | −1 |
| 200 | 29.1 | 37.1 | +23 | −2 |
| 400 | 30.1 | 36.6 | +28 | −3 |
| 800 | 30.6 | 36.8 | +30 | −3 |
| 1600 | 29.8 | 35.0 | +26 | −7 |

TABLE 4

The Effect of TBP on the Binding of $^3$H—Spiperone to Calf Caudate in the Presence of Serum or Buffer.

| | % $^3$H—Spiperone Bound | | % Change | |
|---|---|---|---|---|
| μg/Tube TBP | in Serum | in Buffer | in Serum | in Buffer |
| 0 | 23.7 | 37.1 | 0 | 0 |
| 1.56 | 29.5 | 37.3 | +24 | +1 |
| 3.13 | 30.6 | 36.4 | +29 | −2 |
| 6.25 | 31.6 | 36.0 | +33 | −3 |
| 12.5 | 31.6 | 35.1 | +33 | −5 |
| 25.0 | 31.4 | 29.3 | +32 | −20 |
| 50.0 | 31.5 | 23.7 | +33 | −36 |
| 100.0 | 28.8 | 8.8 | +22 | −76 |

EXAMPLE 3

The Effect of Blocking Agents on "Protein Effect" in a Radioreceptor Assay System for β-Adrenergic Assays By a method similar to that used in Example 2 the effect of blocking agents on serum binding in an assay system for β-adrenergic drugs was determined and compared to results in Tris-HCl buffer.

The assay procedure and reagents used were as described by U'Prichard et al., J. Biol. Chem., 253, 5090–5102 (1978). All solutions were prepared in 50 mM Tris-HCl buffer pH 7.4 hereinafter referred to as "Tris buffer". To glass tubes (12×75 mm) were added human, drug-free serum or Tris buffer (20 μl), $^{125}$I-hydroxybenzylpindolol (HYP) (50 μl, 0.02 nM in Tris-buffer), blocking agent in Tris-buffer (50 μl; concentrations as shown in results) and rat heart membrane (0.7 to 0.9 ml ca. 100 μg of membrane protein) and the tube volume adjusted to 1.0 ml with buffer. The binding reaction was allowed to proceed for 30 minutes at ambient temperature, the reaction mixture filtered, the filter papers washed twice with buffer (10 ml), collected and monitored for radioactivity in a gamma counter. The percentage binding of HYP was determined and the results are shown in Tables 5 to 7 for TBEP, TBP and TEP, respectively.

TABLE 5

The Effect of TBEP on the Binding of $^{125}$I-HYP to β-Adrenergic Receptors in the Presence of Serum or Buffer.

| μg/ml TBEP | $^{125}$I-HYP Bound (CPM) | | % Change | |
|---|---|---|---|---|
| | in Serum | in Buffer | in Serum | in Buffer |
| 0 | 2151 | 8621 | 0 | 0 |
| 0.10 | 2333 | 8513 | +8 | −1 |
| 0.20 | 2526 | 8226 | +17 | −5 |
| 0.50 | 4720 | 8729 | +119 | +1 |
| 1.0 | 5671 | 8510 | +164 | −1 |
| 5.0 | 6133 | 8630 | +185 | 0 |
| 10.0 | 6091 | 8412 | +183 | −2 |

TABLE 6

The Effect of TEP on the Binding of $^{125}$I-HYP to β-Adrenergic Receptors in the Presence of Serum or Buffer.

| mg/ml TEP | $^{125}$I-HYP Bound (CPM) | | % Change | |
|---|---|---|---|---|
| | in Serum | in Buffer | in Serum | in Buffer |
| 0 | 2053 | 8432 | 0 | 0 |
| 0.08 | 3812 | 8367 | +86 | −1 |
| 0.10 | 4131 | 7988 | +101 | −5 |
| 0.50 | 6011 | 7972 | +193 | −5 |
| 1.0 | 5903 | 7931 | +188 | −6 |
| 2.0 | 5881 | 7613 | +186 | −10 |

TABLE 7

The Effect of TBP on the Binding of $^{125}$I-HYP to β-Adrenergic Receptors in the Presence of Serum or Buffer.

| μg/ml TBP | $^{125}$I-HYP Bound (CPM) | | % Change | |
|---|---|---|---|---|
| | in Serum | in Buffer | in Serum | in Buffer |
| 0 | 2011 | 8539 | 0 | 0 |
| 0.10 | 2067 | 8002 | +3 | −6 |
| 0.20 | 2537 | 7987 | +26 | −6 |
| 0.50 | 5853 | 8066 | +191 | −6 |
| 1.0 | 5791 | 8051 | +188 | −6 |
| 5.0 | 5871 | 8091 | +192 | −5 |
| 10.0 | 5863 | 7899 | +192 | −6 |

EXAMPLE 4

The Effect of a Blocking Agent on "Protein Effect" in a Radioreceptor Assay System for Tricyclic Antidepressant Drugs By a procedure similar to that used in Example 2, the effect of TEP on serum effect was determined in a radioreceptor assay for tricyclic antidepressant drugs. The assay employed $^3$H-desipramine as the radio ligand and talc as the receptor. All reagents were prepared in potassium phosphate buffer, pH 7.4, hereinafter referred to as phosphate buffer.

To each glass tube (12×75 mm) was added $^3$H-desipramine (50 μl; final concentration 1.0 nM), triethyl phosphate (TEP) (50 μl; concentrations as shown in the results), human, drug-free serum or phosphate buffer (50 μl) and talc (0.7 to 0.9 ml of a suspension in phosphate buffer, ca. 200 μg talc). The reaction was allowed to proceed for 30 minutes at ambient temperature, the reaction mixture filtered and the filter papers washed with phosphate buffer (2×10 ml) and assayed for $^3$H as described in Example 2. The results are shown in Table 8.

TABLE 8

The Effect of TEP on the Binding of $^3$H—Desipramine to Talc in the Presence of Serum or Buffer.

| μg/ml TEP | $^3$H—Desipramine Bound (CPM) | | % Change | |
|---|---|---|---|---|
| | in Serum | in Buffer | in Serum | in Buffer |
| 0 | 7017 | 12306 | 0 | 0 |
| 50 | 7740 | 12093 | +10 | −2 |
| 100 | 8276 | 11748 | +18 | −5 |
| 500 | 9204 | 13024 | +31 | +6 |
| 750 | 9198 | 11507 | +30 | −6 |
| 1000 | 9745 | 11925 | +39 | −3 |
| 1250 | 10016 | 12362 | +43 | 0 |

A kit may be prepared comprising:
1. Receptor-tracer mixture: A lyophilised mixture of calf caudate (receptor) and $^3$H-spiperone (labelled receptor binder) in a ratio of 8 mg calf caudate to each 0.4 pmole $^3$H-spiperone;
2. Neuroleptic standards: Lyophilised samples of the following amounts of haloperidol in 1 ml samples of human serum: 0, 15 nM, 30 nM, 100 nM, 300 nM, 1000 nM, 100 μM;
3. Blocking Agent: Tris(butoxyethyl) phosphate: 1 ml.

The kit may be use to perform the assay described in Example 2. To carry out this assay the following steps are taken:
1. Dilute TBEP to 30 μg/ml with distilled water;
2. Add the TBEP solution (25 ml) to each sample of receptor-tracer;
3. Add distilled water (1 ml) to each neuroleptic standard;
4. Introduce sample or standard (100 μl) into sample tubes;
5. Add mixture (0.5 ml) from step 2 to each sample tube;
6. Incubate tubes for 30 minutes at 37° C.;
7. Add cold saline (2 ml) to each sample tube;
8. Centrifuge each tube and discard supernatant;
9. Treat residual pellets with scintillant and count for $^3$H in a liquid scintillation spectrometer.

EXAMPLE 6

Beta Blocker Drug Radioreceptor Assay Kit

A kit may be prepared comprising:
1. β Adrenergic Receptor: Lyophilized turkey erythrocyte membranes* (receptor) at ca. 40 μg/ml in 12 mM Tris-HCl pH 7.4, 0.09 M NaCl.
   *Prepared by the method of Minneman, K. P., et al. Molecular Pharmac. 17, 1–7 (1980)
2. Beta Blocker Drug Standards: Lyophilized samples of the following amounts of propranolol (beta blocker drug) in 1 ml of human serum: 0, 4 nM, 8 nM, 16 nM, 32 nM, 64 nM, 10 μM.
3. $^{125}$I-Hydroxybenzylpindolol (HYP): $^{125}$I-HYP (2,200 Ci/mmole) in 12 mM Tris-HCl pH 7.4, 0.09 M NaCl at concentration of 20 pM.
4. Blocking Agent: Tris(butoxyethyl) phosphate: 1 ml The kit may be used to perform the assay as follows:
1. Dilute TBEP to 40 μg/ml with distilled H$_2$O.
2. Add the TBEP solution (25 ml) to each sample of Beta Adrenergic Receptor.
3. Add distilled water (1 ml) to each Beta Blocker Standard.
4. Introduce sample or standard (25 μl) into sample tube.
5. Introduce $^{125}$I-HYP (100 μl) into sample tubes.

6. Add receptor (500 μl) from step 2 to each sample tube.
7. Incubate tubes for 15 minutes at 37° C.
8. Add cold saline (2 ml) to each sample tube.
9. Centrifuge each tube and discard supernatant.
10. Count residual pellets for $^{125}$I in a gamma scintillation spectrometer.

U.S. Pat. No. 4,197,288 discloses the assay procedure and test kit for use with particular basic drugs without the improvement disclosed herein. The entire contents of U.S. Pat. No. 4,197,288 are incorporated herein by reference hereto.

What we may claim may comprise any novel feature described herein principally but not exclusively for example:

(a) A method of assaying a basic drug in a biological fluid said method comprising the steps of:
  (i) adding to the fluid to be assayed a receptor material, a labelled receptor binder (ligand) for the receptor material and a blocking agent selected from a compound of formula (I) as defined herein, the blocking agent being present in an amount sufficient to prevent binding or displace drug or receptor binder from interfering protein but insufficient to prevent binding of drug or receptor binder to the receptor material;
  (ii) causing the drug and receptor binder to interact with the receptor material; and
  (iii) determining the proportion of bound to unbound receptor binder.

(b) An assay test kit comprising:
  a receptor material for a basic drug;
  a labelled receptor binder for the receptor material; and
  a blocking agent as herein defined.

(c) A composition of matter comprising:
  a receptor material for a basic drug;
  a basic drug;
  a labelled receptor binder for a basic drug;
  a blocking agent as herein defined;
  a biological fluid, suitably a human body fluid.

(d) A compound of formula (I) as defined herein for use as a blocking agent in a competitive binding assay for a basic drug.

We claim:

1. The method of determining the concentration of neuroleptic drug and any active metabolites thereof in a body fluid containing same comprising (a) mixing together dopamine receptor material, radioactive dopamine receptor binder, a blocking agent of formula (I)

wherein $R^1$, $R^2$ and $R^3$ are the same or different and are each lower alkyl or lower alkoxy lower alkyl and body fluid, and measuring the amount of the radioactive dopamine receptor binder on the dopamine receptor material and (b) mixing together a concentration of a standard amount of non-radioactive dopamine receptor binder, dopamine receptor material and radioactive dopamine receptor binder and measuring the amount of radioactive dopamine receptor binder on the dopamine receptor material.

2. The method of claim 1 in which the material, binder, blocking agent and body fluid are permitted to remain together a time sufficient to produce sufficient binding of the binder and drug and any active metabolites thereof in the body fluid to said receptor material prior to making the measurement.

3. The method of claim 1 in which the material, binder, blocking agent and body fluid are combined in the presence of sufficient buffer to produce a pH of about 6 to 9.

4. The method of claim 1 in which unbound binder and body fluid are removed as part of the measurement.

5. The method of claim 1 in which the dopamine receptor material is brain tissue, and the radionuclide portion of the binder comprises $^3$H or radioactive iodine.

6. The method of claim 1 in which iodine is $^{125}$I or $^{131}$I.

7. The method of claim 1 in which the concentration of body fluid in the mixture containing same is less than about 15%.

8. The method of claim 7 in which the concentration of body fluid in the mixture containing same is less than about 10%.

9. The method of claim 1 in which radioactive dopamine receptor binder is selected from the group of radioactive labelled haloperidol, pimozide, chlorpromazine, fluphenazine, flupenthixol, spiroperidol, clazapine, thioridazine, fluspirilene, clopenthixol, loxapine, perphenzaine, dopamine and apomorphine.

10. The method of claim 9 in which the radioactive receptor binder is radioactive labelled haloperidol.

11. The method of claim 9 in which the radioactive receptor binder is radioactive labelled spiroperidol.

12. The method of claim 1 in which measuring of the amount of radioactive dopamine binder on the dopamine receptor material is determined in a gamma detector or scintillation counter based upon the nature of the radionuclide portion of the radioactive binder.

13. The method of claim 1 in which the concentration of drug and metabolite in the blood is determined by reference to a standard curve representing percent inhibition of radioactive dopamine-receptor binder vs. non-radioactive dopamine receptor binder.

14. The method of claim 1 in which (b) is repeated a sufficient number of times while varying concentration of the non-radioactive binder to provide information for generating a standard curve.

15. The method of claim 14 in which the radioactive binder is the same in (a) and (b).

16. The method of claim 1 in which the receptor material is brain tissue.

17. The method of claim 1 in which the body fluid is blood plasma or blood serum.

18. The method of measuring the concentration of neuroleptic drug and any active metabolites thereof in blood plasma or blood serum containing same which comprises (a) mixing together blood plasma or blood serum with radioactive dopamine receptor binder, blocking agent of formula (1)

wherein $R^1$, $R^2$ and $R^3$ are the same or different and are each lower alkyl or lower alkoxy lower alkyl and dopamine receptor material and measuring the amount of the radioactive dopamine receptor binder on the dopamine receptor material and (b) mixing together a concentration of a standard amount of non-radioactive dopamine receptor binder, dopamine receptor material and the same radioactive dopamine receptor binder as in (a) and measuring the amount of radioactive dopamine receptor binder on the dopamine receptor material.

19. The method of claim 18 in which measuring of the amount of radioactive dopamine receptor binder on the dopamine receptor material is determined in a gamma detector or scintillation counter based upon the nature of the radionuclide portion of the radioactive binder.

20. The method of claim 19 in which the concentration of drug and active metabolite is determined by reference to a standard curve representing percent inhibition of radioactive dopamine receptor binder vs. non-radioactive dopamine receptor binder.

21. The method of claim 18 in which unbound drug, unbound radioactive binder and plasma or serum are removed as part of determining the percent inhibition of binding.

22. The method of claim 18 in which the concentration of body fluid in the mixture containing same is less than about 15%.

23. The method of claim 22 in which the concentration is less than about 10%.

24. The method of claim 23 in which the amount of body fluid in the mixture containing same is greater than one microliter.

25. The method of claim 18 in which the receptor material is brain tissue.

26. The method of claim 18 in which (b) is repeated a sufficient number of times while varying concentration of the non-radioactive binder to provide information for generating a standard curve.

27. As a mercantile unit, a kit of at least one container of radioactive dopamine receptor binder, dopamine receptor material, protein blocking agent of formula (1)

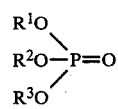

wherein $R^1$, $R^2$ and $R^3$ are the same or different and are each lower alkyl or lower alkoxy lower alkyl and standard non-radioactive dopamine receptor binder.

28. The kit of claim 27 in which the radioactive dopamine receptor binder is selected from the group consisting of radioactive labelled pimozide, chlorpromazine, fluphenazine, flupenthixol, spiroperidol, clozapine, thioridazine, trifluoperazine, fluspirilene, clopenthixol, loxapine, haloperidol, and perphenazine.

29. The kit of claim 28 in which said standard binder is selected from the group consisting of pimozide, chlorpromazine, fluphenazine, flupenthixol, spiroperidol, clozapine, thioridazine, trifluoperazine, fluspirilene, clopenthixol, loxapine, haloperidol and perphenazine.

30. The method of claim 1 in which the blocking agent is selected from triethyl phosphate, tributyl phosphate and tris(butoxyethyl) phosphate.

31. The method of claim 18 in which the blocking agent is selected from triethyl phosphate, tributyl phosphate and tris(butoxyethyl) phosphate.

32. The kit of claim 27 in which the blocking agent is selected from triethyl phosphate, tributyl phosphate and tris(butoxyethyl) phosphate.

33. The method of determining the concentration of a basic drug and any active metabolites thereof in a biological fluid containing same comprising (a) mixing together a receptor material for a basic drug, a labelled receptor binder for said receptor material, a blocking agent of formula (I)

wherein $R^1$, $R^2$ and $R^3$ are the same or different and are each lower alkyl or lower alkoxy lower alkyl and biological fluid, and measuring the amount of the labelled receptor binder on said receptor material and (b) mixing together a concentration of a standard amount of non-labelled receptor binder for said receptor material, said receptor material and labelled receptor binder for said receptor material and measuring the amount of labelled receptor binder on receptor binder.

34. The method of claim 33 in which the receptor material, binder and biological fluid are permitted to remain together a time sufficient to produce sufficient binding of the binder and drug and any active metabolites thereof in the biological fluid to said receptor material prior to making the measurement.

35. In the method of determining basic drug binding to a receptor therefor in a biological fluid containing $\alpha_1$-acid glycoprotein the step of adding a compound of formula (I)

wherein $R^1$, $R^2$ and $R^3$ are the same or different and are each lower alkyl or lower alkoxy lower alkyl whereby the $\alpha_1$-acid glycoprotein binding to the basic drug is inhibited.

36. A method of assaying a basic drug in a biological fluid said method comprising the steps of:
(i) adding to the fluid to be assayed a receptor material, a labelled receptor binder (ligand) for the receptor material and a blocking agent selected from a compound of formula (I) as defined herein, the blocking agent being present in an amount sufficient to prevent binding or displace drug or receptor binder from interfering protein but insufficient to prevent binding of drug or receptor binder to the receptor material;
(ii) causing the drug and receptor binder to interact with the receptor material; and
(iii) determining the proportion of bound to unbound receptor binder.

37. An assay test kit comprising:
a receptor material for a basic drug;
a labelled receptor binder for the receptor material; and
a protein blocking agent herein defined.

38. A composition of matter comprising:
a receptor material for a basic drug;
a basic drug;
a labelled receptor binder for a basic drug;
a protein blocking agent herein defined;
a biological fluid, suitably a human body fluid.

* * * * *